US009249458B1

(12) United States Patent
Benner

(10) Patent No.: US 9,249,458 B1
(45) **Date of Patent: *Feb. 2, 2016**

(54) SELF-AVOIDING MOLECULAR RECOGNITION SYSTEMS IN DNA PRIMING

(71) Applicant: Steven Albert Benner, Gainesville, FL (US)

(72) Inventor: Steven Albert Benner, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/524,227

(22) Filed: Oct. 27, 2014

Related U.S. Application Data

(63) Continuation of application No. 12/229,159, filed on Aug. 20, 2008, now Pat. No. 8,871,469, which is a continuation of application No. 11/647,609, filed on Dec. 30, 2006, now abandoned, which is a continuation of application No. 11/271,366, filed on Nov. 12, 2005, now abandoned.

(60) Provisional application No. 60/627,460, filed on Nov. 13, 2004, provisional application No. 60/627,459, filed on Nov. 13, 2004, provisional application No. 60/654,424, filed on Feb. 18, 2005.

(51) Int. Cl.

| | |
|---|---|
| *C12Q 1/68* | (2006.01) |
| *C12P 19/34* | (2006.01) |
| *C07H 21/02* | (2006.01) |
| *C07H 19/04* | (2006.01) |
| *C07H 21/04* | (2006.01) |

(52) U.S. Cl.
CPC .............. *C12Q 1/6853* (2013.01); *C07H 21/04* (2013.01); *C12Q 1/6848* (2013.01); *C12Q 1/6876* (2013.01); *C12Q 2525/117* (2013.01); *C12Q 2600/16* (2013.01)

(58) Field of Classification Search
CPC . C12Q 1/6853; C12Q 2525/117; C07H 21/04
USPC ....................... 435/6.12, 91.1; 536/23.1, 26.6
See application file for complete search history.

(56) References Cited

U.S. PATENT DOCUMENTS

| | | | | |
|---|---|---|---|---|
| 5,432,272 | A | 7/1995 | Benner | |
| 8,871,469 | B1 * | 10/2014 | Benner et al. | 435/91.1 |

* cited by examiner

*Primary Examiner* — Jezia Riley

(57) ABSTRACT

This invention combines artificially expanded genetic information systems (AEGIS) with self-avoiding molecular recognition systems (SAMRS), in processes that involve template-directed primer extension in highly multiplexed form in mixtures containing large numbers of primers. This process yields extension products, or in its PCR format, amplicons, that have AEGIS tags that can be cleanly captured in highly complex mixtures.

18 Claims, 3 Drawing Sheets

Figure 2 pyDAA
Donor
Acceptor
Acceptor

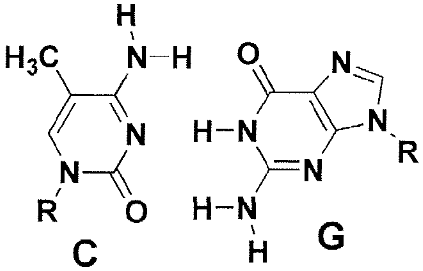

C G puADD
Acceptor
Donor
Donor pyADD
Acceptor
Donor
Donor

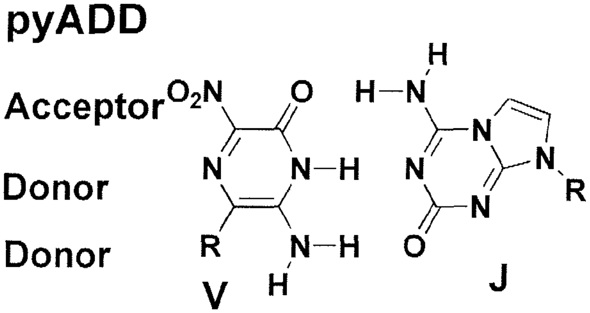

V J puDAA
Donor
Acceptor
Acceptor pyADA
Acceptor
Donor
Acceptor

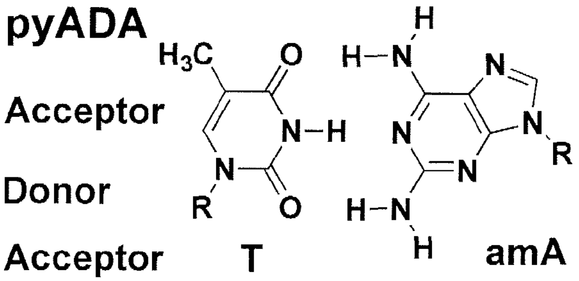

T amA puDAD
Donor
Acceptor
Donor pyDAD
Donor
Acceptor
Donor

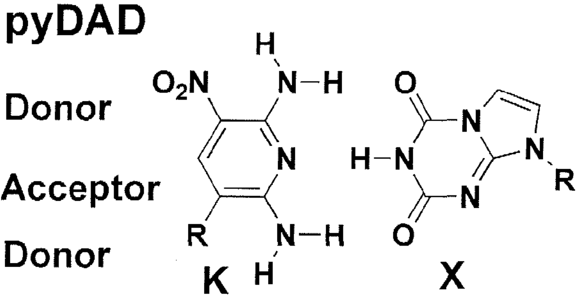

K X puADA
Acceptor
Donor
Acceptor pyAAD
Acceptor
Acceptor
Donor

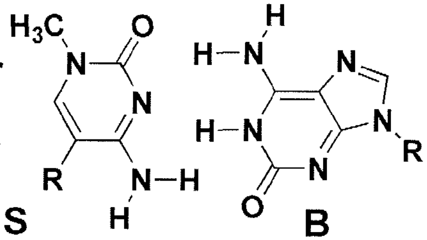

S B puDDA
Donor
Donor
Acceptor pyDDA
Donor
Donor
Acceptor

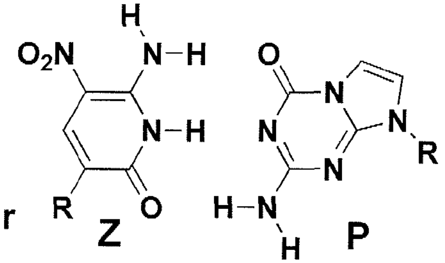

Z P puAAD
Acceptor
Acceptor
Donor

SEQUENCE LISTING

```
<160> NUMBER OF SEQ ID NOS: 60

<210> SEQ ID NO 1
<211> LENGTH: 36
<212> TYPE: DNA
<213> ORGANISM: Artificial Sequence
<220> FEATURE:
```

-continued

<223> OTHER INFORMATION: Synthetic
<220> FEATURE:
<221> NAME/KEY: misc_feature
<222> LOCATION: (4)..(17)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (32)..(32)
<223> OTHER INFORMATION: n = hypoxanthine
<220> FEATURE:
<221> NAME/KEY: misc_feature
<222> LOCATION: (33)..(33)
<223> OTHER INFORMATION: n = 2-aminopurine
<220> FEATURE:
<221> NAME/KEY: misc_feature
<222> LOCATION: (34)..(35)
<223> OTHER INFORMATION: n = 2-thiothymine

<400> SEQUENCE: 1
ctantccncc ancnanccgc gtgttgtcct tnnnng 36

<210> SEQ ID NO 2
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (33)..(33)
<223> OTHER INFORMATION: n = 2-aminopurine
<220> FEATURE:
<221> NAME/KEY: misc_feature
<222> LOCATION: (34)..(34)
<223> OTHER INFORMATION: n = 2-thiothymine
<220> FEATURE:
<221> NAME/KEY: misc_feature
<222> LOCATION: (35)..(36)
<223> OTHER INFORMATION: n = N4-ethylcytidine or
1-(beta-D-2'-deoxyribofuranosyl)-5-methyl-pyrimidin-2-one

<400> SEQUENCE: 2
cagnaagngg tngntngcac acctctccat cgnnnna 37

<210> SEQ ID NO 3
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one

<400> SEQUENCE: 3
annttcacan caattnctcc 20

<210> SEQ ID NO 4
<211> LENGTH: 34
<212> TYPE: DNA
<213> ORGANISM: Artificial Sequence
<220> FEATURE:

-continued

<223> OTHER INFORMATION: Synthetic
<220> FEATURE:
<221> NAME/KEY: misc_feature
<222> LOCATION: (4)..(16)
<223> OTHER INFORMATION: n =
2-amino-8-(1'-beta-D-2'-deoxyribofuranosyl)-imidazo[1,2-a]-1,3,5-triazin-4(8H)one
<220> FEATURE:
<221> NAME/KEY: misc_feature
<222> LOCATION: (30)..(30)
<223> OTHER INFORMATION: n = hypoxanthine
<220> FEATURE:
<221> NAME/KEY: misc_feature
<222> LOCATION: (31)..(32)
<223> OTHER INFORMATION: n = N4-ethylcytidine or
1-(beta-D-2'-deoxyribofuranosyl)-5-methyl-pyrimidin-2-one
<220> FEATURE:
<221> NAME/KEY: misc_feature
<222> LOCATION: (33)..(33)
<223> OTHER INFORMATION: n = 2-aminopurine

<400> SEQUENCE: 4
ctcntccncc ancnancgac caacgtcagn nnnc 34

<210> SEQ ID NO 5
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(16)
<223> OTHER INFORMATION: n =
2-amino-8-(1'-beta-D-2'-deoxyribofuranosyl)-imidazo[1,2-a]-1,3,5-triazin-4(8H)one
<220> FEATURE:
<221> NAME/KEY: misc_feature
<222> LOCATION: (35)..(35)
<223> OTHER INFORMATION: n = 2-thiothymine
<220> FEATURE:
<221> NAME/KEY: misc_feature
<222> LOCATION: (36)..(36)
<223> OTHER INFORMATION: n = 2-aminopurine
<220> FEATURE:
<221> NAME/KEY: misc_feature
<222> LOCATION: (37)..(37)
<223> OTHER INFORMATION: n = hypoxanthine
<220> FEATURE:
<221> NAME/KEY: misc_feature
<222> LOCATION: (38)..(38)
<223> OTHER INFORMATION: n = 2-thiothymine

<400> SEQUENCE: 5
cagnaagngg tngntngggg tctcctctaa cctcnnnnc 39

<210> SEQ ID NO 6
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(16)
<223> OTHER INFORMATION: n =
2-amino-8-(1'-beta-D-2'-deoxyribofuranosyl)-imidazo[1,2-a]-1,3,5-triazin-4(8H)one

<400> SEQUENCE: 6
cacnncccaa ncctcntcta 20

<210> SEQ ID NO 7

-continued

```
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(16)
<223> OTHER INFORMATION: n =
      2-amino-8-(1'-beta-D-2'-deoxyribofuranosyl)-imidazo[1,2-a]-1,3,5-
      triazin-4(8H)one
<220> FEATURE:
<221> NAME/KEY: misc_feature
<222> LOCATION: (30)..(30)
<223> OTHER INFORMATION: n = 2-thiothymine
<220> FEATURE:
<221> NAME/KEY: misc_feature
<222> LOCATION: (31)..(32)
<223> OTHER INFORMATION: n = hypoxanthine
<220> FEATURE:
<221> NAME/KEY: misc_feature
<222> LOCATION: (33)..(33)
<223> OTHER INFORMATION: n = 2-aminopurine

<400> SEQUENCE: 7

ctantccncc ancnanctgg cacgtaggcn nnng                                  34


<210> SEQ ID NO 8
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(16)
<223> OTHER INFORMATION: n =
      2-amino-8-(1'-beta-D-2'-deoxyribofuranosyl)-imidazo[1,2-a]-1,3,5-
      triazin-4(8H)one
<220> FEATURE:
<221> NAME/KEY: misc_feature
<222> LOCATION: (34)..(34)
<223> OTHER INFORMATION: n =  N4-ethylcytidine or
      1-(beta-D-2'-deoxyribofuranosyl)-5-methyl-pyrimidin-2-one
<220> FEATURE:
<221> NAME/KEY: misc_feature
<222> LOCATION: (35)..(35)
<223> OTHER INFORMATION: n = 2-aminopurine
<220> FEATURE:
<221> NAME/KEY: misc_feature
<222> LOCATION: (36)..(36)
<223> OTHER INFORMATION: n = 2-thiothymine
<220> FEATURE:
<221> NAME/KEY: misc_feature
<222> LOCATION: (37)..(37)
<223> OTHER INFORMATION: n = hypoxanthine

<400> SEQUENCE: 8

cagnaagngg tngntngcag acagcacctt tagnnnnc                              38

<210> SEQ ID NO 9
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(18)
<223> OTHER INFORMATION: n =
      2-amino-8-(1'-beta-D-2'-deoxyribofuranosyl)-imidazo[1,2-a]-1,3,5-
      triazin-4(8H)one

<400> SEQUENCE: 9

canaccanaa atnccacct                                                   19
```

-continued

<210> SEQ ID NO 10
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (33)..(34)
<223> OTHER INFORMATION: n = 2-aminopurine
<220> FEATURE:
<221> NAME/KEY: misc_feature
<222> LOCATION: (35)..(35)
<223> OTHER INFORMATION: n = 2-thiothymine
<220> FEATURE:
<221> NAME/KEY: misc_feature
<222> LOCATION: (36)..(36)
<223> OTHER INFORMATION: n = N4-ethylcytidine or
1-(beta-D-2'-deoxyribofuranosyl)-5-methyl-pyrimidin-2-one

<400> SEQUENCE: 10
ctantccncc ancnancgtg cattggtctg cannnng 37

<210> SEQ ID NO 11
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (32)..(32)
<223> OTHER INFORMATION: n = 2-aminopurine
<220> FEATURE:
<221> NAME/KEY: misc_feature
<222> LOCATION: (33)..(35)
<223> OTHER INFORMATION: n = hypoxanthine

<400> SEQUENCE: 11
cagnaagngg tngntngcca tattgacgcc cnnnnt 36

<210> SEQ ID NO 12
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one

<400> SEQUENCE: 12
nancnattan cananaactn ac 22

<210> SEQ ID NO 13
<211> LENGTH: 40
<212> TYPE: DNA
<213> ORGANISM: Artificial Sequence -continued
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (36)..(36)
<223> OTHER INFORMATION: n = 2-aminopurine
<220> FEATURE:
<221> NAME/KEY: misc_feature
<222> LOCATION: (37)..(37)
<223> OTHER INFORMATION: n = N4-ethylcytidine or
1-(beta-D-2'-deoxyribofuranosyl)-5-methyl-pyrimidin-2-one
<220> FEATURE:
<221> NAME/KEY: misc_feature
<222> LOCATION: (38)..(38)
<223> OTHER INFORMATION: n = hypoxanthine
<220> FEATURE:
<221> NAME/KEY: misc_feature
<222> LOCATION: (39)..(39)
<223> OTHER INFORMATION: n = N4-ethylcytidine or
1-(beta-D-2'-deoxyribofuranosyl)-5-methyl-pyrimidin-2-one

<400> SEQUENCE: 13
ctantccncc ancnancgtc tttcaatatg ctgaannnng 40

<210> SEQ ID NO 14
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (33)..(34)
<223> OTHER INFORMATION: n = hypoxanthine
<220> FEATURE:
<221> NAME/KEY: misc_feature
<222> LOCATION: (35)..(36)
<223> OTHER INFORMATION: n = 2-aminopurine

<400> SEQUENCE: 14
ctantccncc ancnancgag gccacaaacc atnnnng 37

<210> SEQ ID NO 15
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (36)..(36)
<223> OTHER INFORMATION: n = 2-aminopurine
<220> FEATURE:
<221> NAME/KEY: misc_feature
<222> LOCATION: (37)..(37)
<223> OTHER INFORMATION: n = N4-ethylcytidine or
1-(beta-D-2'-deoxyribofuranosyl)-5-methyl-pyrimidin-2-one -continued <220> FEATURE:
<221> NAME/KEY: misc_feature
<222> LOCATION: (38)..(38)
<223> OTHER INFORMATION: n = hypoxanthine
<220> FEATURE:
<221> NAME/KEY: misc_feature
<222> LOCATION: (39)..(39)
<223> OTHER INFORMATION: n = N4-ethylcytidine or
1-(beta-D-2'-deoxyribofuranosyl)-5-methyl-pyrimidin-2-one

<400> SEQUENCE: 15
ctantccncc ancnancgtc tatcaatatg ctgaannnng 40

<210> SEQ ID NO 16
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (30)..(30)
<223> OTHER INFORMATION: n = 2-aminopurine
<220> FEATURE:
<221> NAME/KEY: misc_feature
<222> LOCATION: (31)..(31)
<223> OTHER INFORMATION: n = hypoxanthine
<220> FEATURE:
<221> NAME/KEY: misc_feature
<222> LOCATION: (32)..(32)
<223> OTHER INFORMATION: n = N4-ethylcytidine or
1-(beta-D-2'-deoxyribofuranosyl)-5-methyl-pyrimidin-2-one
<220> FEATURE:
<221> NAME/KEY: misc_feature
<222> LOCATION: (33)..(33)
<223> OTHER INFORMATION: n = 2-thiothymine

<400> SEQUENCE: 16
ctantccncc ancnancatg cgccacggan nnng 34

<210> SEQ ID NO 17
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (36)..(36)
<223> OTHER INFORMATION: n = N4-ethylcytidine or
1-(beta-D-2'-deoxyribofuranosyl)-5-methyl-pyrimidin-2-one
<220> FEATURE:
<221> NAME/KEY: misc_feature
<222> LOCATION: (37)..(37)
<223> OTHER INFORMATION: n = 2-thiothymine
<220> FEATURE:
<221> NAME/KEY: misc_feature
<222> LOCATION: (38)..(38)
<223> OTHER INFORMATION: n = hypoxanthine
<220> FEATURE:
<221> NAME/KEY: misc_feature
<222> LOCATION: (39)..(39)
<223> OTHER INFORMATION: n = 2-thiothymine

<400> SEQUENCE: 17
cagnaagngg tngntngtga gaatctcttc gccaannnng 40

<210> SEQ ID NO 18
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (32)..(32)
<223> OTHER INFORMATION: n = 2-thiothymine
<220> FEATURE:
<221> NAME/KEY: misc_feature
<222> LOCATION: (33)..(34)
<223> OTHER INFORMATION: n = 2-aminopurine
<220> FEATURE:
<221> NAME/KEY: misc_feature
<222> LOCATION: (35)..(35)
<223> OTHER INFORMATION: n = N4-ethylcytidine or
1-(beta-D-2'-deoxyribofuranosyl)-5-methyl-pyrimidin-2-one

<400> SEQUENCE: 18
cagnaagngg tngntnggga ggggtctcct cnnnnc 36

<210> SEQ ID NO 19
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(20)
<223> OTHER INFORMATION: n =
2-amino-8-(1'-beta-D-2'-deoxyribofuranosyl)-imidazo[1,2-a]-1,3,5-
triazin-4(8H)one

<400> SEQUENCE: 19
cnanaaaccn cntntcaact 20

<210> SEQ ID NO 20
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: n =
2-amino-8-(1'-beta-D-2'-deoxyribofuranosyl)-imidazo[1,2-a]-1,3,5-
triazin-4(8H)one

<400> SEQUENCE: 20
cncatnncnt antnnactan 20

<210> SEQ ID NO 21
<211> LENGTH: 19
<212> TYPE: DNA
<213> ORGANISM: Artificial Sequence
<220> FEATURE:
<223> OTHER INFORMATION: Synthetic -continued
<220> FEATURE:
<221> NAME/KEY: misc_feature
<222> LOCATION: (2)..(20)
<223> OTHER INFORMATION: n =
      2-amino-8-(1'-beta-D-2'-deoxyribofuranosyl)-imidazo[1,2-a]-1,3,5-
      triazin-4(8H)one

<400> SEQUENCE: 21
anaaaccntn tntcaactn 19

<210> SEQ ID NO 22
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n =
      2-amino-8-(1'-beta-D-2'-deoxyribofuranosyl)-imidazo[1,2-a]-1,3,5-
      triazin-4(8H)one

<400> SEQUENCE: 22
ncntnncata ttnnactanc 20

<210> SEQ ID NO 23
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
      2-amino-8-(1'-beta-D-2'-deoxyribofuranosyl)-imidazo[1,2-a]-1,3,5-
      triazin-4(8H)one
<220> FEATURE:
<221> NAME/KEY: misc_feature
<222> LOCATION: (30)..(30)
<223> OTHER INFORMATION: n = N4-ethylcytidine or
      1-(beta-D-2'-deoxyribofuranosyl)-5-methyl-pyrimidin-2-one
<220> FEATURE:
<221> NAME/KEY: misc_feature
<222> LOCATION: (31)..(32)
<223> OTHER INFORMATION: n = 2-aminopurine
<220> FEATURE:
<221> NAME/KEY: misc_feature
<222> LOCATION: (33)..(33)
<223> OTHER INFORMATION: n = N4-ethylcytidine or
      1-(beta-D-2'-deoxyribofuranosyl)-5-methyl-pyrimidin-2-one

<400> SEQUENCE: 23
ctantccncc ancnanctga tcgccattcn nnnc 34

<210> SEQ ID NO 24
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
      2-amino-8-(1'-beta-D-2'-deoxyribofuranosyl)-imidazo[1,2-a]-1,3,5-
      triazin-4(8H)one
<220> FEATURE:
<221> NAME/KEY: misc_feature
<222> LOCATION: (34)..(35)
<223> OTHER INFORMATION: n = 2-aminopurine
<220> FEATURE:

-continued

<221> NAME/KEY: misc_feature
<222> LOCATION: (36)..(36)
<223> OTHER INFORMATION: n = 2-thiothymine
<220> FEATURE:
<221> NAME/KEY: misc_feature
<222> LOCATION: (37)..(37)
<223> OTHER INFORMATION: n = N4-ethylcytidine or
1-(beta-D-2'-deoxyribofuranosyl)-5-methyl-pyrimidin-2-one

<400> SEQUENCE: 24
cagnaagngg tngntngggt gtcatcacac atannnnc 38

<210> SEQ ID NO 25
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one

<400> SEQUENCE: 25
ntcnnattcn anccattnac 20

<210> SEQ ID NO 26
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (34)..(34)
<223> OTHER INFORMATION: n = 2-aminopurine
<220> FEATURE:
<221> NAME/KEY: misc_feature
<222> LOCATION: (35)..(35)
<223> OTHER INFORMATION: n = N4-ethylcytidine or
1-(beta-D-2'-deoxyribofuranosyl)-5-methyl-pyrimidin-2-one
<220> FEATURE:
<221> NAME/KEY: misc_feature
<222> LOCATION: (36)..(36)
<223> OTHER INFORMATION: n = 2-aminopurine
<220> FEATURE:
<221> NAME/KEY: misc_feature
<222> LOCATION: (37)..(37)
<223> OTHER INFORMATION: n = hypoxanthine

<400> SEQUENCE: 26
ctantccncc ancnanccaa gaacccagtt gacnnnng 38

<210> SEQ ID NO 27
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one -continued <220> FEATURE:
<221> NAME/KEY: misc_feature
<222> LOCATION: (35)..(36)
<223> OTHER INFORMATION: n = N4-ethylcytidine or
      1-(beta-D-2'-deoxyribofuranosyl)-5-methyl-pyrimidin-2-one
<220> FEATURE:
<221> NAME/KEY: misc_feature
<222> LOCATION: (37)..(37)
<223> OTHER INFORMATION: n = hypoxanthine
<220> FEATURE:
<221> NAME/KEY: misc_feature
<222> LOCATION: (38)..(38)
<223> OTHER INFORMATION: n = 2-thiothymine

<400> SEQUENCE: 27
cagnaagngg tngntngggg aacaaatgga ttgannnnc 39

<210> SEQ ID NO 28
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
      2-amino-8-(1'-beta-D-2'-deoxyribofuranosyl)-imidazo[1,2-a]-1,3,5-
      triazin-4(8H)one

<400> SEQUENCE: 28
nanaacctac atnatctcac tcc 23

<210> SEQ ID NO 29
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
      2-amino-8-(1'-beta-D-2'-deoxyribofuranosyl)-imidazo[1,2-a]-1,3,5-
      triazin-4(8H)one
<220> FEATURE:
<221> NAME/KEY: misc_feature
<222> LOCATION: (37)..(37)
<223> OTHER INFORMATION: n = 2-aminopurine
<220> FEATURE:
<221> NAME/KEY: misc_feature
<222> LOCATION: (38)..(39)
<223> OTHER INFORMATION: n = 2-thiothymine
<220> FEATURE:
<221> NAME/KEY: misc_feature
<222> LOCATION: (40)..(40)
<223> OTHER INFORMATION: n = N4-ethylcytidine or
      1-(beta-D-2'-deoxyribofuranosyl)-5-methyl-pyrimidin-2-one

<400> SEQUENCE: 29
ctantccncc ancnancctg agagcggatc atttacnnnn c 41

<210> SEQ ID NO 30
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
      2-amino-8-(1'-beta-D-2'-deoxyribofuranosyl)-imidazo[1,2-a]-1,3,5-

-continued triazin-4(8H)one
<220> FEATURE:
<221> NAME/KEY: misc_feature
<222> LOCATION: (36)..(36)
<223> OTHER INFORMATION: n = 2-aminopurine
<220> FEATURE:
<221> NAME/KEY: misc_feature
<222> LOCATION: (37)..(37)
<223> OTHER INFORMATION: n = N4-ethylcytidine or
1-(beta-D-2'-deoxyribofuranosyl)-5-methyl-pyrimidin-2-one
<220> FEATURE:
<221> NAME/KEY: misc_feature
<222> LOCATION: (38)..(38)
<223> OTHER INFORMATION: n = 2-thiothymine
<220> FEATURE:
<221> NAME/KEY: misc_feature
<222> LOCATION: (39)..(39)
<223> OTHER INFORMATION: n = hypoxanthine

<400> SEQUENCE: 30
cagnaagngg tngntngcaa tctcctttgc aggtannnnc 40

<210> SEQ ID NO 31
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one

<400> SEQUENCE: 31
ncttttaanc tncanntctn c 21

<210> SEQ ID NO 32
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (35)..(36)
<223> OTHER INFORMATION: n = 2-thiothymine
<220> FEATURE:
<221> NAME/KEY: misc_feature
<222> LOCATION: (37)..(37)
<223> OTHER INFORMATION: n = hypoxanthine
<220> FEATURE:
<221> NAME/KEY: misc_feature
<222> LOCATION: (38)..(38)
<223> OTHER INFORMATION: n = 2-thiothymine

<400> SEQUENCE: 32
ctantccncc ancnanccag tagcgattcc actgnnnnc 39

<210> SEQ ID NO 33
<211> LENGTH: 41
<212> TYPE: DNA
<213> ORGANISM: Artificial Sequence
<220> FEATURE:
<223> OTHER INFORMATION: Synthetic
<220> FEATURE:

-continued

<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (37)..(37)
<223> OTHER INFORMATION: n = hypoxanthine
<220> FEATURE:
<221> NAME/KEY: misc_feature
<222> LOCATION: (38)..(38)
<223> OTHER INFORMATION: n = 2-thiothymine
<220> FEATURE:
<221> NAME/KEY: misc_feature
<222> LOCATION: (39)..(40)
<223> OTHER INFORMATION: n = N4-ethylcytidine or
1-(beta-D-2'-deoxyribofuranosyl)-5-methyl-pyrimidin-2-one

<400> SEQUENCE: 33
cagnaagngg tngntnggag tcatttccca tttcttnnnn c 41

<210> SEQ ID NO 34
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one

<400> SEQUENCE: 34
nctnacanct ttanacacca c 21

<210> SEQ ID NO 35
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (35)..(35)
<223> OTHER INFORMATION: n = 2-aminopurine
<220> FEATURE:
<221> NAME/KEY: misc_feature
<222> LOCATION: (36)..(37)
<223> OTHER INFORMATION: n = hypoxanthine
<220> FEATURE:
<221> NAME/KEY: misc_feature
<222> LOCATION: (38)..(38)
<223> OTHER INFORMATION: n = N4-ethylcytidine or
1-(beta-D-2'-deoxyribofuranosyl)-5-methyl-pyrimidin-2-one
<220> FEATURE:
<221> NAME/KEY: misc_feature
<222> LOCATION: (38)..(38)
<223> OTHER INFORMATION: n = N4-ethylcytidine or
1-(beta-D-2'-deoxyribofuranosyl)-5-methyl-pyrimidin-2-one

<400> SEQUENCE: 35
ctantccncc ancnanccaa gaacatagcc tctannnng 39
<210> SEQ ID NO 36
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (36)..(36)
<223> OTHER INFORMATION: n = 2-aminopurine
<220> FEATURE:
<221> NAME/KEY: misc_feature
<222> LOCATION: (37)..(37)
<223> OTHER INFORMATION: n = N4-ethylcytidine or
1-(beta-D-2'-deoxyribofuranosyl)-5-methyl-pyrimidin-2-one
<220> FEATURE:
<221> NAME/KEY: misc_feature
<222> LOCATION: (38)..(38)
<223> OTHER INFORMATION: n = 2-thiothymine
<220> FEATURE:
<221> NAME/KEY: misc_feature
<222> LOCATION: (39)..(39)
<223> OTHER INFORMATION: n = hypoxanthine

<400> SEQUENCE: 36
cagnaagngg tngntnggcg tacacatctt ggtatnnnnc 40

<210> SEQ ID NO 37
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one

<400> SEQUENCE: 37
tntatncaca canacnccac 20

<210> SEQ ID NO 38
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (33)..(33)
<223> OTHER INFORMATION: n = hypoxanthine
<220> FEATURE:
<221> NAME/KEY: misc_feature
<222> LOCATION: (34)..(34)
<223> OTHER INFORMATION: n = 2-aminopurine
<220> FEATURE:
<221> NAME/KEY: misc_feature
<222> LOCATION: (35)..(35)
<223> OTHER INFORMATION: n = hypoxanthine
<220> FEATURE:
<221> NAME/KEY: misc_feature
<222> LOCATION: (36)..(36)
<223> OTHER INFORMATION: n = 2-thiothymine

<400> SEQUENCE: 38
ctantccncc ancnanccgg catgattgca aannnnc 37

<210> SEQ ID NO 39
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (36)..(36)
<223> OTHER INFORMATION: n = 2-thiothymine
<220> FEATURE:
<221> NAME/KEY: misc_feature
<222> LOCATION: (37)..(37)
<223> OTHER INFORMATION: n = 2-aminopurine
<220> FEATURE:
<221> NAME/KEY: misc_feature
<222> LOCATION: (38)..(38)
<223> OTHER INFORMATION: n = 2-thiothymine
<220> FEATURE:
<221> NAME/KEY: misc_feature
<222> LOCATION: (39)..(39)
<223> OTHER INFORMATION: n = N4-ethylcytidine or
1-(beta-D-2'-deoxyribofuranosyl)-5-methyl-pyrimidin-2-one

<400> SEQUENCE: 39
cagnaagngg tngntngcgg agcttatggc aacttnnnnc 40

<210> SEQ ID NO 40
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one

<400> SEQUENCE: 40
ntttnancna cactnctana ac 22

<210> SEQ ID NO 41
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (35)..(35)
<223> OTHER INFORMATION: n = 2-aminopurine
<220> FEATURE:
<221> NAME/KEY: misc_feature
<222> LOCATION: (36)..(36)
<223> OTHER INFORMATION: n = 2-thiothymine
<220> FEATURE:

```
<221> NAME/KEY: misc_feature
<222> LOCATION: (37)..(37)
<223> OTHER INFORMATION: n = N4-ethylcytidine or
      1-(beta-D-2'-deoxyribofuranosyl)-5-methyl-pyrimidin-2-one
<220> FEATURE:
<221> NAME/KEY: misc_feature
<222> LOCATION: (38)..(38)
<223> OTHER INFORMATION: n = hypoxanthine

<400> SEQUENCE: 41

ctantccncc ancnanccaa cgatcttacc atccnnnng                        39


<210> SEQ ID NO 42
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
      2-amino-8-(1'-beta-D-2'-deoxyribofuranosyl)-imidazo[1,2-a]-1,3,5-
      triazin-4(8H)one
<220> FEATURE:
<221> NAME/KEY: misc_feature
<222> LOCATION: (37)..(37)
<223> OTHER INFORMATION: n = N4-ethylcytidine or
      1-(beta-D-2'-deoxyribofuranosyl)-5-methyl-pyrimidin-2-one
<220> FEATURE:
<221> NAME/KEY: misc_feature
<222> LOCATION: (38)..(38)
<223> OTHER INFORMATION: n = 2-aminopurine
<220> FEATURE:
<221> NAME/KEY: misc_feature
<222> LOCATION: (39)..(40)
<223> OTHER INFORMATION: n = 2-thiothymine

<400> SEQUENCE: 42

cagnaagngg tngntngcca ttgttccaat gaatgcnnnn g                     41


<210> SEQ ID NO 43
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
      2-amino-8-(1'-beta-D-2'-deoxyribofuranosyl)-imidazo[1,2-a]-1,3,5-
      triazin-4(8H)one

<400> SEQUENCE: 43

canananaac tcataannan cac                                         23


<210> SEQ ID NO 44
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
      2-amino-8-(1'-beta-D-2'-deoxyribofuranosyl)-imidazo[1,2-a]-1,3,5-
      triazin-4(8H)one
<220> FEATURE:
<221> NAME/KEY: misc_feature
<222> LOCATION: (1)..(24)
<223> OTHER INFORMATION: n =
```

-continued 2-amino-8-(1'-beta-D-2'-deoxyribofuranosyl)-imidazo[1,2-a]-1,3,5-
triazin-4(8H)one

<400> SEQUENCE: 44
ncaccatcat aaatccaatt ncana 25

<210> SEQ ID NO 45
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(24)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (34)..(34)
<223> OTHER INFORMATION: n = hypoxanthine
<220> FEATURE:
<221> NAME/KEY: misc_feature
<222> LOCATION: (35)..(35)
<223> OTHER INFORMATION: n = N4-ethylcytidine or
1-(beta-D-2'-deoxyribofuranosyl)-5-methyl-pyrimidin-2-one
<220> FEATURE:
<221> NAME/KEY: misc_feature
<222> LOCATION: (36)..(36)
<223> OTHER INFORMATION: n = 2-aminopurine
<220> FEATURE:
<221> NAME/KEY: misc_feature
<222> LOCATION: (37)..(37)
<223> OTHER INFORMATION: n = 2-thiothymine

<400> SEQUENCE: 45
ctantccncc ancnanccac agagtcaagc aagnnnng 38

<210> SEQ ID NO 46
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(24)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (35)..(36)
<223> OTHER INFORMATION: n = 2-thiothymine
<220> FEATURE:
<221> NAME/KEY: misc_feature
<222> LOCATION: (37)..(38)
<223> OTHER INFORMATION: n = 2-aminopurine

<400> SEQUENCE: 46
cagnaagngg tngntngggc ctccttttcc ccatnnnng 39

<210> SEQ ID NO 47
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(24)
<223> OTHER INFORMATION: n =

```
      2-amino-8-(1'-beta-D-2'-deoxyribofuranosyl)-imidazo[1,2-a]-1,3,5-
      triazin-4(8H)one

<400> SEQUENCE: 47

natntcacan aannttncan c                                           21


<210> SEQ ID NO 48
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(24)
<223> OTHER INFORMATION: n =
      2-amino-8-(1'-beta-D-2'-deoxyribofuranosyl)-imidazo[1,2-a]-1,3,5-
      triazin-4(8H)one
<220> FEATURE:
<221> NAME/KEY: misc_feature
<222> LOCATION: (34)..(36)
<223> OTHER INFORMATION: n = 2-aminopurine
<220> FEATURE:
<221> NAME/KEY: misc_feature
<222> LOCATION: (37)..(37)
<223> OTHER INFORMATION: n = hypoxanthine

<400> SEQUENCE: 48

ctantccncc ancnancgtg aggacgagtc acannnng                         38


<210> SEQ ID NO 49
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
      2-amino-8-(1'-beta-D-2'-deoxyribofuranosyl)-imidazo[1,2-a]-1,3,5-
      triazin-4(8H)one
<220> FEATURE:
<221> NAME/KEY: misc_feature
<222> LOCATION: (37)..(38)
<223> OTHER INFORMATION: n = 2-thiothymine
<220> FEATURE:
<221> NAME/KEY: misc_feature
<222> LOCATION: (39)..(39)
<223> OTHER INFORMATION: n = hypoxanthine
<220> FEATURE:
<221> NAME/KEY: misc_feature
<222> LOCATION: (40)..(40)
<223> OTHER INFORMATION: n = N4-ethylcytidine or
      1-(beta-D-2'-deoxyribofuranosyl)-5-methyl-pyrimidin-2-one

<400> SEQUENCE: 49

cagnaagngg tngntnggag atagatttct acaccgnnnn c                     41


<210> SEQ ID NO 50
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
      2-amino-8-(1'-beta-D-2'-deoxyribofuranosyl)-imidazo[1,2-a]-1,3,5-
      triazin-4(8H)one

<400> SEQUENCE: 50
```

natcaananc actntcatca atcc 24

<210> SEQ ID NO 51
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (34)..(34)
<223> OTHER INFORMATION: n = 2-aminopurine
<220> FEATURE:
<221> NAME/KEY: misc_feature
<222> LOCATION: (35)..(35)
<223> OTHER INFORMATION: n = hypoxanthine
<220> FEATURE:
<221> NAME/KEY: misc_feature
<222> LOCATION: (36)..(36)
<223> OTHER INFORMATION: n = 2-thiothymine
<220> FEATURE:
<221> NAME/KEY: misc_feature
<222> LOCATION: (37)..(37)
<223> OTHER INFORMATION: n = 2-aminopurine

<400> SEQUENCE: 51
ctantccncc ancnanccca agagcctgaa ggannnng 38

<210> SEQ ID NO 52
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (35)..(35)
<223> OTHER INFORMATION: n = 2-thiothymine
<220> FEATURE:
<221> NAME/KEY: misc_feature
<222> LOCATION: (36)..(36)
<223> OTHER INFORMATION: n = hypoxanthine
<220> FEATURE:
<221> NAME/KEY: misc_feature
<222> LOCATION: (37)..(37)
<223> OTHER INFORMATION: n = 2-aminopurine
<220> FEATURE:
<221> NAME/KEY: misc_feature
<222> LOCATION: (38)..(38)
<223> OTHER INFORMATION: n = 2-thiothymine

<400> SEQUENCE: 52
cagnaagngg tngntngcct tacttatggg agccnnnng 39

<210> SEQ ID NO 53
<211> LENGTH: 22
<212> TYPE: DNA
<213> ORGANISM: Artificial Sequence
<220> FEATURE:
<223> OTHER INFORMATION: Synthetic
<220> FEATURE:

<221> NAME/KEY: misc_feature
<222> LOCATION: (1)..(24)
<223> OTHER INFORMATION: n =
2-amino-8-(1'-beta-D-2'-deoxyribofuranosyl)-imidazo[1,2-a]-1,3,5-
triazin-4(8H)one

<400> SEQUENCE: 53
nacactncca natcattctt nc 22

<210> SEQ ID NO 54
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(24)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (34)..(34)
<223> OTHER INFORMATION: n = hypoxanthine
<220> FEATURE:
<221> NAME/KEY: misc_feature
<222> LOCATION: (35)..(35)
<223> OTHER INFORMATION: n = 2-aminopurine
<220> FEATURE:
<221> NAME/KEY: misc_feature
<222> LOCATION: (36)..(36)
<223> OTHER INFORMATION: n = 2-thiothymine
<220> FEATURE:
<221> NAME/KEY: misc_feature
<222> LOCATION: (37)..(37)
<223> OTHER INFORMATION: n = N4-ethylcytidine or
1-(beta-D-2'-deoxyribofuranosyl)-5-methyl-pyrimidin-2-one

<400> SEQUENCE: 54
ctantccncc ancnanccgg tgcaaatgga tttnnnnc 38

<210> SEQ ID NO 55
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(24)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (33)..(36)
<223> OTHER INFORMATION: n = 2-thiothymine

<400> SEQUENCE: 55
cagnaagngg tngntnggag agcagctttg gcnnnng 37

<210> SEQ ID NO 56
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(24)
<223> OTHER INFORMATION: n =
2-amino-8-(1'-beta-D-2'-deoxyribofuranosyl)-imidazo[1,2-a]-1,3,5- triazin-4(8H)one

<400> SEQUENCE: 56
cnatcanttt ntcttcantt annatc 26

<210> SEQ ID NO 57
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(24)
<223> OTHER INFORMATION: n =
2-amino-8-(1'-beta-D-2'-deoxyribofuranosyl)-imidazo[1,2-a]-1,3,5-
triazin-4(8H)one

<400> SEQUENCE: 57
cttacanccn ttanaatctt cttcc 25

<210> SEQ ID NO 58
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(24)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (34)..(34)
<223> OTHER INFORMATION: n = 2-aminopurine
<220> FEATURE:
<221> NAME/KEY: misc_feature
<222> LOCATION: (35)..(35)
<223> OTHER INFORMATION: n = hypoxanthine
<220> FEATURE:
<221> NAME/KEY: misc_feature
<222> LOCATION: (36)..(36)
<223> OTHER INFORMATION: n = N4-ethylcytidine or
1-(beta-D-2'-deoxyribofuranosyl)-5-methyl-pyrimidin-2-one
<220> FEATURE:
<221> NAME/KEY: misc_feature
<222> LOCATION: (37)..(37)
<223> OTHER INFORMATION: n = 2-thiothymine

<400> SEQUENCE: 58
ctantccncc ancnancctg aaggatgtag agcnnnng 38

<210> SEQ ID NO 59
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(24)
<223> OTHER INFORMATION: n =
2-amino-8-(1'-beta-D-2'-deoxyribofuranosyl)-imidazo[1,2-a]-1,3,5-
triazin-4(8H)one
<220> FEATURE:
<221> NAME/KEY: misc_feature
<222> LOCATION: (36)..(37)
<223> OTHER INFORMATION: n = N4-ethylcytidine or
1-(beta-D-2'-deoxyribofuranosyl)-5-methyl-pyrimidin-2-one
<220> FEATURE:
<221> NAME/KEY: misc_feature -continued

```
<222> LOCATION: (38)..(38)
<223> OTHER INFORMATION: n = 2-aminopurine
<220> FEATURE:
<221> NAME/KEY: misc_feature
<222> LOCATION: (39)..(39)
<223> OTHER INFORMATION: n = 2-thiothymine

<400> SEQUENCE: 59

cagnaagngg tngntnggcc gaattcatta gaggannnnc                          40


<210> SEQ ID NO 60
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(24)
<223> OTHER INFORMATION: n =
      2-amino-8-(1'-beta-D-2'-deoxyribofuranosyl)-imidazo[1,2-a]-1,3,5-
      triazin-4(8H)one

<400> SEQUENCE: 60

canaanttcn ntnttanact tcc                                             23
```

SELF-AVOIDING MOLECULAR RECOGNITION SYSTEMS IN DNA PRIMING

Continuation in part of U.S. patent application Ser. No. 12/229,159 filed 2008 Aug. 20 Which is a Continuation in part of U.S. patent application Ser. No. 11/647,609 filed 2008 Dec. 30 Which is a Continuation in part of U.S. patent application Ser. No. 11/271,366 filed 2005 Nov. 12 Which is based on provisional patent applications 60/627,460 and 60/627,459 filed 2004 Nov. 13 and 60/654,424 filed 2005 Dec. 20

This invention was made with government support under W911NF12C0059 awarded by The Office of the Secretary of Defense US Army RDECOM ACQ CTR. The government may have certain rights in the invention.

FIELD

This invention relates to the field of nucleic acid chemistry, more specifically to the field of compositions and processes that can serve as primers for the copying of DNA and RNA. Most specifically, this invention relates to compositions of matter that bind to natural DNA and RNA following simple rules as they serve as primers, without binding as strongly to themselves.

BACKGROUND

Scientists have long sought innovative molecular recognition systems that have binding properties that are useful in different ways. The structures of these systems have been modeled to resemble the structures of DNA and RNA which, in their polymeric form, are called "oligonucleotides". Further, as with DNA and RNA, the molecular recognition systems have been useful because they bind to other components of the molecular recognition systems and/or to natural DNA and RNA following rules that can be expressed in a form that guides practitioners of ordinary skill in the art and enables them to do useful things.

DNA serves as an archetype to illustrate both molecular structure and rule base recognition. With DNA, three rules (A pairs with T, G pairs with C, the strands are antiparallel) permit the design of two DNA molecules that bind to each other in aqueous solution. When the rules are perfectly followed, two perfectly complementary DNA strands of a substantial length (15-20 nucleotides is normally sufficient in physiological buffers at 37° C.) will bind to each other with substantial selectivity even in complex mixtures containing many other DNA molecules. Heuristic rules have been developed over the years to permit the prediction of general trends in DNA:DNA binding affinity. These have come by performing substantial numbers of melting temperature experiments. For examples as heuristic rules, longer DNA strands generally bind to their partners with higher melting temperatures ($T_m$s) than shorter strands. G:C pairs generally contribute more to duplex stability than A:T pairs. More highly parameterized models improve on the estimates of melting temperatures [All98a] [All98b] [Mar85] [Mat98]. While it remains true that the precise stability of duplexes may not be predictable, that imprecision does not defeat the utility of DNA: DNA binding or require undue experimentation to exploit, even though the number of different DNA sequences of length n (=$4^n$) that would fall within a patent for the DNA molecular recognition system would be enormous.

It has been argued that this rule-based behavior arises because of the repeating charge in the backbone of nucleic acids [Ben04]. Certainly, analogs that have that repeating charges in their backbone maintain their rule-based pairing behavior even if they become quite long. In contrast, the few examples of useful nucleic acid analogs that lack a repeating charge in their backbone do not maintain their rule-based binding behavior in polymers built from two-dozen or more monomer units (fewer if the nucleobases are predominately guanine). The archetypal example of such an uncharged DNA analog is the peptide nucleic acids (PNAs) [Egh92], where rule-based molecular recognition does not survive in longer molecules.

Artificially Expanded Genetic Information Systems (AEGIS)

An archetype of a human-invented rule-based molecular recognition is the artificially expanded genetic information system (AEGIS) disclosed in U.S. Pat. No. 5,432,272. The design of this artificial molecular recognition system began with the observation that two principles of complementarity govern the Watson-Crick pairing of nucleic acids: size complementarity (large purines pair with small pyrimidines) and hydrogen bonding complementarity (hydrogen bond donors from one nucleobase pair with hydrogen bond acceptors from the other). These two principles give rise to the simple rules for base pairing ("A pairs with T, G pairs with C") that underlie genetics, molecular biology, and biotechnology.

U.S. Pat. No. 5,432,272 pointed out that these principles can be met by nucleotides other than adenine (A) and thymine (T), and guanine (G) and cytosine (C). Rather, twelve nucleobases forming six base pairs joined by mutually exclusive hydrogen bonding patterns might be possible within the geometry of the Watson-Crick base pair. FIG. 1 shows some of the standard and non-standard nucleobase pairs, together with the nomenclature to designate them. Those nucleobase analogs presenting non-standard hydrogen bonding patterns are part of an Artificially Expanded Genetic Information System, or AEGIS.

U.S. Pat. No. 5,432,272 and subsequent patents all taught that the hydrogen bonding pattern that makes an AEGIS component useful as a unit of molecular recognition is distinguishable from the heterocycle that implements it. This means that different heterocycles can often serve interchangeably as molecular recognition elements. This, in turn, permits the elements of an artificial molecular recognition system to be chosen based on considerations other than simple recognition. Thus, the pyADA hydrogen bonding pattern in AEGIS is implemented by thymidine, uridine, uridine derivatives carrying a 5-position linker attached to a fluorescent moiety, uridine derivatives carrying a 5-position linker attached to a biotin, and pseudouridine, for example.

Four features of the AEGIS system make it suited for application:

(a) AEGIS supports rule-based design. Anyone of ordinary skill in the art can design two AEGIS-containing molecules that bind to each other, after learning only a few additional rules, just as they can design binding partners with standard DNA. Again, a critical mass of melting temperatures were collected to support heuristic rules that allow prediction of affinity. As with DNA, the precise $T_m$s are not predictable even with these heuristic rules, but this imprecision does not defeat the utility of the system, or create a need for undue experimentation to design AEGIS pairing partners.

(b) This rule-based molecular recognition displayed by AEGIS is orthogonal to that displayed by standard DNA. If two strands incorporating standard DNA bases are mixed with two other strands incorporating AEGIS components, the first pair will bind to each other only, and the second pair will bind to each other only, without formation of hybrids between the strands containing canonical and non-canonical bases. This allows two molecular recognition processes to occur independently in the same vessel.

(c) Sequences built from AEGIS components have higher information density (more different sequences per unit length), especially when they incorporate the full 12 letters that the AEGIS technology allows. This allows fewer near-mismatches in complicated systems to slow hybridization, for example. Thus, AEGIS tags hybridize more quickly [Col97].

(d) Enzymes can be found that allow AEGIS systems to be manipulated in ways common in biotechnology with standard DNA. These enzymes include polymerases that do primer extension, copy templates that contain AEGIS components, and amplify AEGIS oligonucleotides a polymerase chain reaction (PCR). Here, undue experimentation is often required to obtain enzymes that do this effectively, as many natural enzymes regard non-standard nucleotides as "foreign", and do not accept them or, if they do, do not accept them with useful affinity.

An archetypal application of AEGIS is in the branched DNA (bDNA) assay used to measure levels of HIV, hepatitis B, and hepatitis C viruses in human patients [Elb04a] [Elb04b)]. As this example shows, even though the behavior of DNA duplexes built from AEGIS components having different sequences are not identical and may not be precisely predictable, this has not prevented the AEGIS molecular recognition system from improving the health care of some 400,000 patients annually [Ben04]. This is an illustration of the utility of orthogonality in the analytical chemistry of nucleic acids.

Self Avoiding Molecular Recognition Systems (SAMRS)

A self-avoiding molecular recognition system (SAMRS) has components that bind to natural DNA or RNA, but not to other components of the same unnatural system. In its general description, a SAMRS incorporates nucleobase analogs that replace T, A, G, and C by analogs that are indicated as T*, A*, G*, and C*, which are collectively called "* analogs" of T, A, G, and C respectively. In the simplest implementation of this concept, these * analogs are each able to form two hydrogen bonds to the complementary A, T, C, and G. This means that the T*:A, A*:T, C:*G, and G*:C nucleobase pairs contribute to duplex stability to approximately the same extent as an A:T pair. A SAMRS obtains its self-avoiding properties because the hydrogen bonding groups of the * analogs are chosen the T*:A* and C*:G* nucleobase pairs do not contribute as much to duplex stability because (in the simplest implementation) they are joined by only one hydrogen bond.

As with standard DNA, standard RNA, and oligonucleotides that add non-standard nucleobase pairing, within predicting the binding properties of any sequence within a SAMRS system will be subject to the same imprecision as predicting the properties of an arbitrary DNA or RNA molecule. Thus, as a general rule, if individuals of ordinary skill in the art wish to design a SAMRS sequence that binds to a preselected standard DNA molecule with a Tm of 25° C., they would write down the preselected sequence in the 5'-to-3' direction, and then write below the SAMRS sequence in an antiparallel direction, matching a T* against every A in the preselected sequence, an A* against every T in the preselected sequence, a C* against every G in the preselected sequence, and a G* against every C in the preselected sequence. It is an open question as to whether such simple instructions allow one of ordinary skill in the art to obtain useful outcomes without undue experimentation. As elaborated below, attempts to obtain such utility failed when we took instruction from the prior art. One object of the instant invention is to provide SAMRS components that provide utility based on precisely this simple a set of rules and instructions.

The need for self-avoiding behaviors has long been pressing when an experimentalist sought to have mixtures containing more than two oligonucleotides, and especially pressing when making libraries of oligonucleotides (defined as having 10 or more oligonucleotide components), especially when those oligonucleotides were to interact with enzymes such as DNA polymerases. This problem is exemplified by multiplexed PCR, where the amplification is sought of many segments of DNA in one pot. This is attempted by adding in large excess two primers flanking each segment, contacting mixture with nucleoside triphosphates, and cycling the mixture up and down in temperature in the presence of a thermostable DNA polymerase. At low temperatures, the primers anneal to the template. At higher temperatures, the polymerase extends the primer to make a product copy of the template. At the highest temperature, the product copy falls off the template, allowing more primers to bind when the temperature is dropped. The primers compete with full length product copies for their binding sites on the template by being present in high concentrations.

While PCR can be successfully multiplexed up to a dozen or so amplicons, with careful design to avoid having the primers present in high concentrations interact with each other, eventually even the most careful design does not prevent primer-primer interactions. These create undesired amplicons, primer dimers, and other artifacts that defeat the utility of the PCR.

BRIEF DESCRIPTION OF THE DRAWINGS

FIG. 2. Another "artificially expanded genetic information system (AEGIS). Twelve nucleobases in a nucleic acid alphabet that form specific pairs with the constraints of the Watson-Crick geometry. Note different implementations of the same hydrogen bonding pattern in many cases, including the addition of an amino group to complete the hydrogen bonding pattern of standard adenosine, by making the nucleobase diaminopurine.

SUMMARY OF THE INVENTION

This invention combines AEGIS with SAMRS, where a tag containing one or more AEGIS nucleotides is appended to the 5'-end of the molecules that are claimed in the parent application, U.S. patent application Ser. No. 12/229,159, which is incorporated herein in its entirety by reference. This tag has utility, for example, by allowing multiplexed primer extension that is directed by templates built from only natural nucleotides to yield products that have tags that contain one or more AEGIS nucleotides, and therefore do not fully complement any natural oligonucleotide. It also has utility in a process for multiplexed nested PCR of multiple targets [Bro97], where the product amplicons carry one or more tags that contain one or more AEGIS nucleotides, and therefore do not fully complement any natural oligonucleotide.

DETAILED DESCRIPTION OF THE INVENTION

The goal of the instant invention is to provide primers that could be extended by DNA polymerases when templated on a natural DNA, and to provide primers that could support PCR (which requires that a primer, after being extended, must also be accepted as a template by a DNA polymerase), where the products of these processes have an AEGIS tag.

With both SAMRS and AEGIS, the instant invention teaches a distinction between the hydrogen bonding pattern of a SAMRS system and the heterocycle used to implement it. As is well known in the art, appendages may be attached the 5-position of pyrimidines without interfering with the hydrogen bonding that supports duplex formation. Indeed, 5-position alkyl, allyl, and acetylenic substituents at those positions generally encourage duplex formation. Likewise, substituents at this position may carry tags useful for capture (such as biotin) or detection (such as fluorescent species). The instant invention teaches that similar substituents can be attached at the "5-equivalent" position of the heterocycle that implements the SAMRS and AEGIS, noting that the IUPAC numbering of the heterocycle may assign a different numbering to the 5-equivalent position of any given heterocycle.

Analogous substitutions may be placed at the 7-equivalent position of a 7-deazapurine analog that is a part of a SAMRS and AEGIS. Further, the 7-equivalent nitrogen may be replaced by a CH unit simply to prevent Hoogsteen binding.

Likewise, while 2'-deoxyribose is the preferred backbone when it is desired to have the SAMRS component be recognized by natural DNA polymerases, RNA polymerases, and reverse transcriptases, tighter binding is obtained by placing the SAMRS- and AEGIS-enabling heterocycles on 2'-OMe, 2'-O-alkyl, and/or 2'-O-allyl ribose, PNA, or LNA, which are all taught here as part of the instant invention (such disclosure not being obvious without such a teaching).

Figure 3:
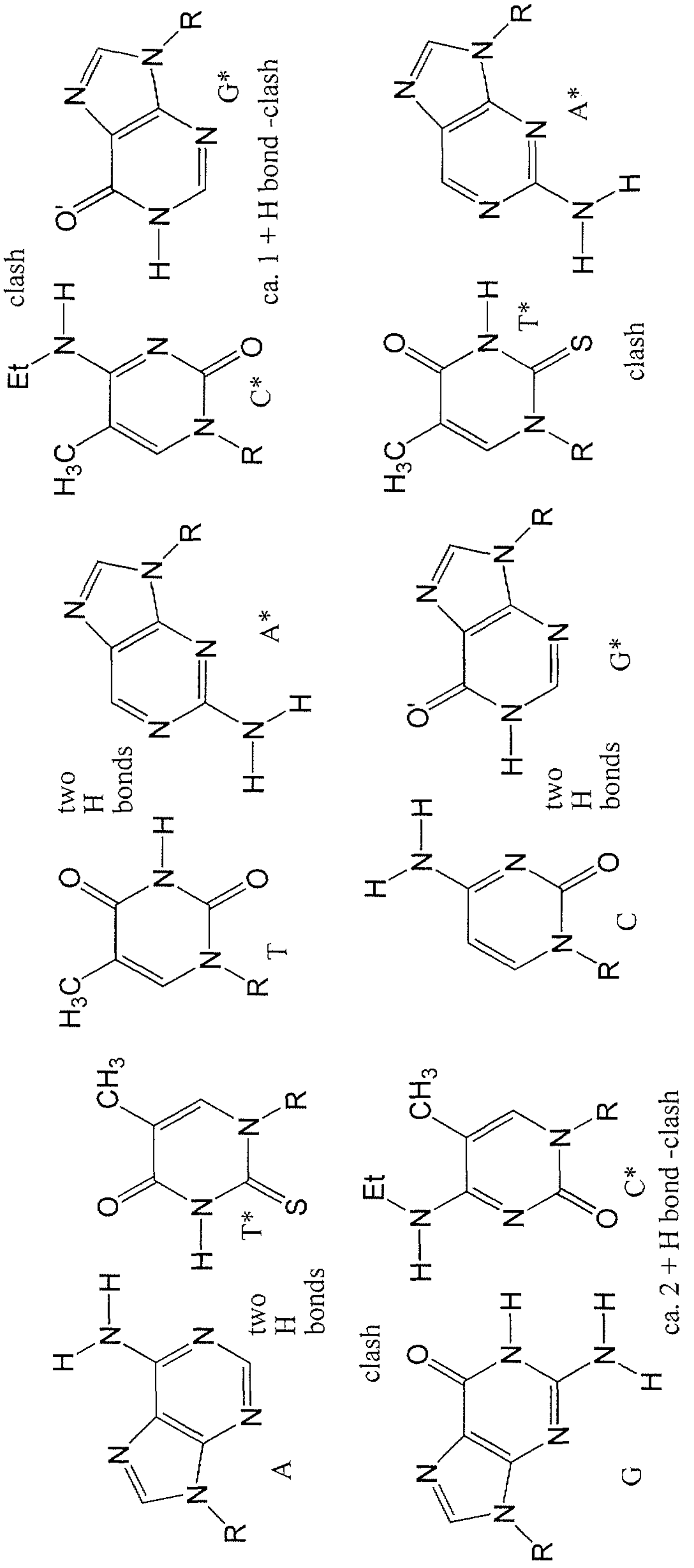
FIG. 3. Self-Avoiding Molecular Recognition System (SAMRS) in their presently preferred implementation. A molecular recognition system that binds to complementary natural DNA, but not to complementary SAMRS sequences. The pairing of each of the complements of the SAMRS heterocycles (denoted by an asterisk *) with a standard nucleobase is joined by two hydrogen bonds, while pairs between any two size-complementary SAMRS components are joined by (at most) one hydrogen bond. Note that the G*-C* and A*-T* pairs in the wobble structure do not have two productive hydrogen bonds. Diaminopurine (not shown) is a presently preferred alternative implementation of A*.

The discussion of the inventive steps by which the presently preferred implementations of the SAMRS concept were developed is provided in U.S. patent application Ser. No. 12/229,159, of which this is a continuation-in-part. U.S. patent application Ser. No. 12/229,159 is incorporated in its entirety by reference. The presently preferred implementations of the SAMRS heterocycles are in FIG. 3.

As noted in U.S. patent application Ser. No. 12/229,159, reduction to practice discovered as an unexpected phenomenon that the melting temperatures of duplexes supported by only base pairs joined by two hydrogen bonds were abnormally low. Thus, while the 2-thioT:A pair was modestly more stable on average (with the metric being a higher Tm in a variety of contexts) than the T:A pair, a fact well known in the literature, and the I:C pair was significantly less stable than the G:C pair (a fact also well known), duplexes joined by only 2-thioT:A, 2-AP:T, I:C, and $^{4Et}$C:G pairs were significantly less stable than expected.

This observation prompted the exploration of primers having the self-avoiding property at the 3'-end of the primer more than at the 5'-end of the primer, as it is overlap of the 3'-ends of primers in primer libraries that causes primer-primer interactions that defeat the PCR analysis. Thus, this would direct one of ordinary skill in the art to place standard nucleobases at the 5'-end.

As a consequence, rules were developed that give the presently preferred embodiments for the primer segments. The preferred 5'-end of the primer is a moiety commonly used in primers, including without limitation OH (the 5'-OH group is free), O-phosphate (allowing the 5'-end to be ligatable), O-oligonucleotide, —$NH_2$, or a phosphate or an amino group linked to a biotin or a fluorescent tag. The 3'-terminal nucleotide preferably has one of the standard nucleotides, adenine (or diaminopurine), thymine, guanine, cytosine, or uracil, or one of the A*, T*, G*, and C* nucleobases, with the most preferred application being a standard nucleotide at the 3'-end. The SAMRS-containing segment next in from the 3'-end is preferably 4 to 6 nucleotides in length, and entirely composed of A*, T*, G*, and C* nucleotides, although a single standard nucleotide can be in segment. The next segments, proceeding away from the 3'-end, are presently preferred to be constructed exclusively from A, T, G, and C, although single SAMRS nucleotides in this region can function as well, preferably if they are thiothymidine or thiouracil. This segment is chosen to give a desired affinity to its complement, and is preferably 10 to 20 nucleotides long. In any case, the presently preferred sum of these two segments primers is at least 15, so as to achieve useful affinity to a target oligonucleotide.

These segments, including the 3'-nucleotide, the SAMRS-rich segment, and the SAMRS-poor segments, are designed to be substantially complementary to a portion of the sequence of a target oligonucleotides, to which it will hybridize in the claimed process.

Figure 1:
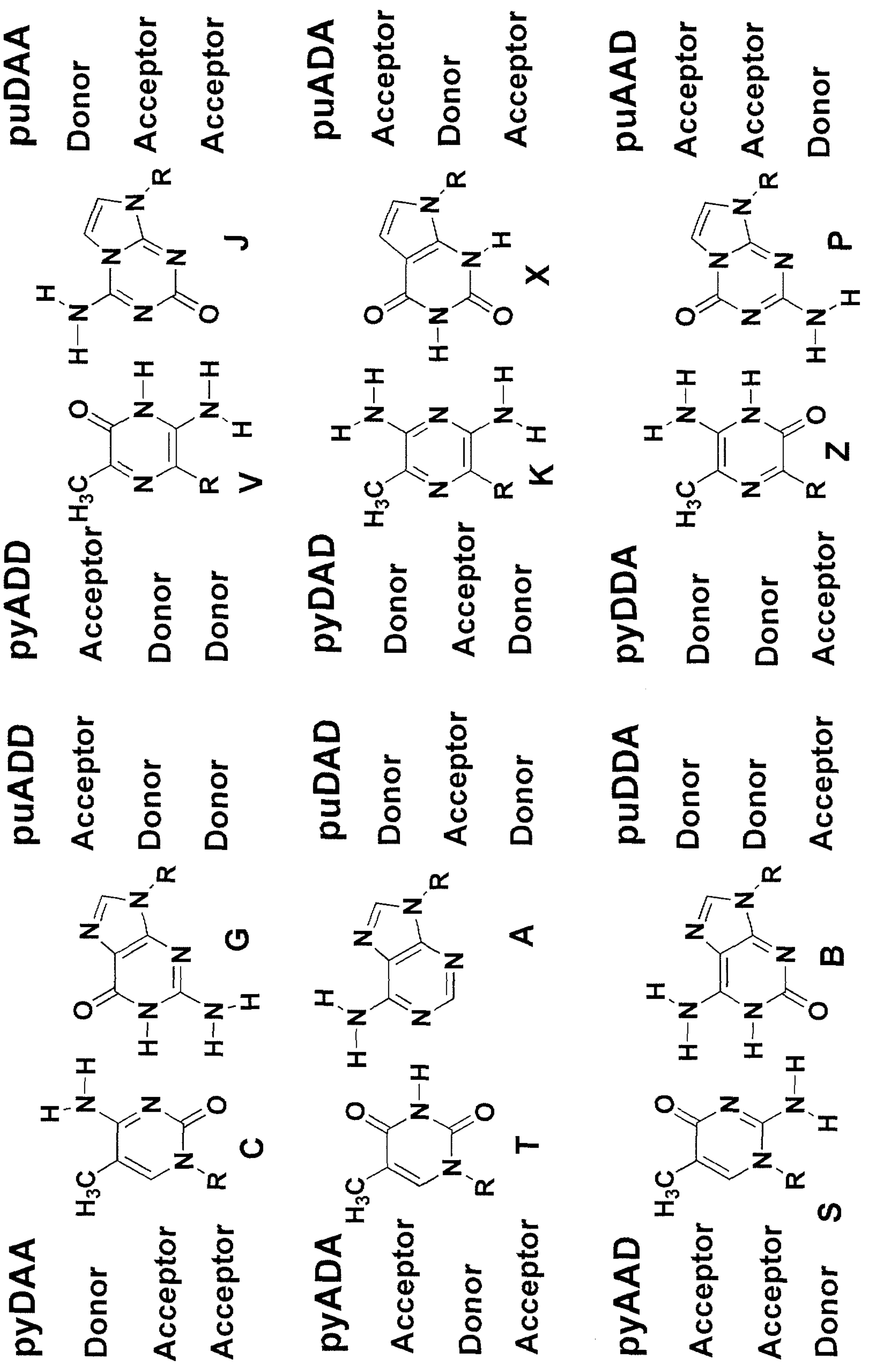
FIG. 1. An "artificially expanded genetic information system (AEGIS). Twelve nucleobases in a nucleic acid alphabet that form specific pairs with the constraints of the Watson-Crick geometry. Pyrimidine base analogs are designated "py", purine by "pu". Upper case letters following a designation indicate the hydrogen bonding pattern of acceptor (A) and donor (D) groups. Thus, cytosine is pyDAA.

The preferred AEGIS tag contains nucleobases independently selected from the group consisting of A, T, G, C, K, X, V, J, S, B, Z and P, wherein K, X, V, J, S, B, Z and P are the nucleobases disclosed in FIG. 1 or FIG. 2. The tag must contain at least one K, X, V, J, S, B, Z and P, but more preferably it contains at least two, and is preferably 5 to 30 nucleotides long.

EXAMPLES

Example 1

Multiplexed Detection of Mosquito-Borne Arboviruses

Mosquito-borne arboviruses must be detected in public health surveillance environments. This example combined the self avoiding molecular recognition system (SAMRS), which enables high levels of multiplexing, with an artificially expanded genetic information system (AEGIS), which enables very clean PCR amplification in nested PCR formats. Luminex "liquid microarrays" were exploited for downstream multiplexed detection.

Targets

This example showed this combination supporting single-tube PCR amplification assays to seek RNA from 21 mosquito-borne RNA viruses from the genera Flavivirus, Alphavirus, and Orthobunyavirus. This assay differentiated between many closely-related viral targets, including dengue, West Nile, Japanese encephalitis, and the California serological group viruses.

TABLE 1

Viruses targeted.

| Family/Genus | Viruses and abbreviations | Primer identity |
|---|---|---|
| Flaviviridae/<br>*Flavivirus*<br>Group IV,<br>positive ssRNA | West Nile (WN) | Forward-WNm1, Reverse-WNm1 |
| | Japanese encephalitis (JE) | Forward-JE m1, Reverse-JE m1 |
| | Saint Louis encephalitis (SLE) | Forward-SLEVm1, Reverse-SLEVm1 |
| | Yellow fever (YF) | Forward-YF m3, Reverse-YF m3 |
| | Dengue serotype 1 (D1) | Forward-D1, Reverse-Den (1, 3) |
| | Dengue serotype 2 (D2) | Forward-D2, Reverse-D (2, 4) |
| | Dengue serotype 3 (D3) | Forward-D3, Reverse-D (1, 3) |
| | Dengue serotype 4 (D4) | Forward-D4, Reverse-D (2, 4) |
| | Murray valley encephalitis (MVE) | Forward-MVE, Reverse-MVE |
| | Rocio (Rocio) | Forward-Rocio, Reverse-Rocio |
| Togaviridae/<br>*Alphavirus*<br>Group IV,<br>positive ssRNA | Eastern Equine Encephalitis (EEE) | Forward-EEEm1, Reverse-EEEm1 |
| | Venezuelan Equine Encephalitis (VEE) | Forward-VEEm1, Reverse-VEEm1 |
| | Western Equine Encephalitis (WEE) | Forward-WEEm1, Reverse-WEEm1 |
| Bunyaviridae/<br>*Orthobunyavirus*<br>Group V<br>negative ssRNA | California encephalitis (CE) | Forward-CE, Reverse-CE |
| | Jamestown Canyon | Forward-JTC Reverse-JTC |
| | La Crosse encephalitis (LAC) | Forward-LAC, Reverse-LAC |
| | Keystone (KS) | Forward-KS, Reverse-KS |
| | Snowshoe Hare (SSH) | Forward-SSH, Reverse-SSH |
| | San Angelo (SA) | Forward2-CAcom, Reverse 1-CAcom |
| | Serra do Navio (SN) | Forward2-CAcom, Reverse 1-CA-com |
| | Melao (Mel) | Forward-Mel, Reverse-Mel |

Primers and Probes

Primers and capture probes containing artificial SAMRS and AEGIS nucleotides (Table 2) were synthesized on ABI 394 and ABI 3900 synthesizers in-house. Primers and capture probes were designed to complement a majority of the strains from each of the target viruses. For the simulants, ssDNA oligonucleotides (Amplimers, Appendix A. Supplementary data Table 2) were chosen arbitrarily to represent a single strain.

TABLE 2

Hybrid SAMRES-AEGIS primers and AEGIS (APTC) probes used in this study. All reverse primers are 5'-biotinylated; the probes are 5'-amino-C12- modified. The AEGIS tags in the primers are underlined.

| Oligos primers/probes | Sequences 5'-3' | Genome Region | GB Accession No. |
|---|---|---|---|
| Forward WNm1 primer | CTAPTCCPCCAPCPAPC<br>CGCGTGTTGTCCTTG*A*T*T*G | 163-181 | NC-009942<br>SEQ ID NO 1 |
| Reverse WNm1 primer | CAGPAAGPGGTPGPTPG<br>CACACCTCTCCATCGA*T*C*C*A | 312-293 | NC-009942<br>SEQ ID NO 2 |
| WN probe | APPTTCACAPCAATTPCTCC | 259-278 | NC-009942<br>SEQ ID NO 3 |
| Forward JE m1 primer | CTAPTCCPCCAPCPAPC<br>GACCAACGTCAGG*C*C*A*C | 10612-10628 | NC_001437<br>SEQ ID NO 4 |
| Reverse JE m1 primer | CAGPAAGPGGTPGPTPG<br>GGGTCTCCTCTAACCTCT*A*G*T*C | 10769-10748 | NC_001437<br>SEQ ID NO 5 |
| JE probe | CACPPCCCAAPCCTCPTCTA | 10705-10724 | NC_001437<br>SEQ ID NO 6 |
| Forward SLE m1 primer | CTAPTCCPCCAPCPAPC<br>TGGCACGTAGGCT*G*G*A*G | 10561-10577 | NC_007580<br>SEQ ID NO 7 |
| Reverse SLEm1 primer | CAGPAAGPGGTPGPTPG<br>CAGACAGCACCTTTAGC*A*T*G*C | 10634-10614 | NC_007580<br>SEQ ID NO 8 |
| SLE probe | CAPACCAPAAATPCCACCT | 10591-10610 | NC_007580<br>SEQ ID NO 9 |
| Forward YF m3 primer | CTAPTCCPCCAPCPAPC<br>GTGCATTGGTCTGCAA*A*T*C*G | 25-44 | NC_002031<br>SEQ ID NO 10 |
| Reverse YF m3 primer | CAGPAAGPGGTPGPTPG<br>CCATATTGACGCCCA*G*G*G*T | 164-146 | NC_002031<br>SEQ ID NO 11 |
| YF probe | PAPCPATTAPCAPAPAACTPAC | 91-112 | NC_002031<br>SEQ ID NO 12 |

TABLE 2-continued

Hybrid SAMRES-AEGIS primers and AEGIS (APTC) probes used in this study. All reverse primers are 5'-biotinylated; the probes are 5'-amino-C12- modified. The AEGIS tags in the primers are underlined.

| Oligos primers/probes | Sequences 5'-3' | Genome Region | GB Accession No. |
|---|---|---|---|
| Forward D1 primer | CTAPTCCPCCAPCPAPC GTCTTTCAATATGCTGAAA*C*G*C*G | 105-127 | FJ639679.1 SEQ ID NO 13 |
| Forward D2 primer | CTAPTCCPCCAPCPAPC GAGGCCACAAACCATG*G*A*A*G | 10433-10452 | EU482570.1 SEQ ID NO 14 |
| Forward D3 primer | CTAPTCCPCCAPCPAPC GTCTATCAATATGCTGAAA*C*G*C*G | 103-128 | EU482596.1 SEQ ID NO 15 |
| Forward D4 primer | CTAPTCCPCCAPCPAPC ATGCGCCACGGAA*G*C*T*G | 10363-10379 | GQ199883.1 SEQ ID NO 16 |
| Reverse D (1,3) primer | CAGPAAGPGGTPGPTPG TGAGAATCTCTTCGCCAAC*T*G*T*G | 174-152 (D1) | FJ639679.1 SEQ ID NO 17 |
| Reverse D (2,4) primer | CAGPAAGPGGTPGPTPG GGAGGGGTCTCCTCT*A*A*C*C | 10497-10479 (D2) | EU482570.1 SEQ ID NO 18 |
| D1 probe | CPAPAAACCPCPTPTCAACT | 128-147 | FJ639679.1 SEQ ID NO 19 |
| D2 probe | CPCATPPCPTAPTPPACTAP | 10457-10476 | EU482570.1 SEQ ID NO 20 |
| D3 probe | APAAACCPTPTPTCAACTPP | 131-151 | EU482596.1 SEQ ID NO 21 |
| D4 probe | PCPTPPCATATTPPACTAPC | 10383-10402 | GQ199883.1 SEQ ID NO 22 |
| Forward MVE primer | CTAPTCCPCCAPCPAPC TGATCGCCATTCC*A*A*C*C | 535-551 | NC_000943 SEQ ID NO 23 |
| Reverse MVE primer | CAGPAAGPGGTPGPTPG GGTGTCATCACACATAA*A*T*C*C | 614-594 | NC_000943 SEQ ID NO 24 |
| MVE probe | PTCPPATTCPAPCCATTPAC | 571-590 | NC_000943 SEQ ID NO 25 |
| Forward-Rocio primer | CTAPTCCPCCAPCPAPC CAAGAACCCAGTTGACA*C*A*G*G | 1883-1903 | AY632542 SEQ ID NO 26 |
| Reverse-Rocio primer | CAGPAAGPGGTPGPTPG GGGAACAAATGGATTGAC*C*G*T*C | 2036-2015 | AY632542 SEQ ID NO 27 |
| Rocio probe | PAPAACCTACATPATCTCACTCC | 1977-1999 | AY632542 SEQ ID NO 28 |
| Forward-EEEm1 primer | CTAPTCCPCCAPCPAPC CTGAGAGCGGATCATTTACA*T*T*C*C | 11034-11057 | NC_003899 SEQ ID NO 29 |
| Reverse-EEEm1 primer | CAGPAAGPGGTPGPTPG CAATCTCCTTTGCAGGTAA*C*T*G*C | 11133-11111 | NC_003899 SEQ ID NO 30 |
| EEE probe | PCTTTTAAPCTPCAPPTCTPC | 11084-11104 | NC_003899 SEQ ID NO 31 |
| Forward-VEEm1 primer | CTAPTCCPCCAPCPAPC CAGTAGCGATTCCACTGT*T*G*T*C | 4339-4360 | NC_001449 SEQ ID NO 32 |
| Reverse-VEEm1 primer | CAGPAAGPGGTPGPTPG GAGTCATTTCCCATTTCTTG*T*C*C*C | 4485-4462 | NC_001449 SEQ ID NO 33 |
| VEE probe | PCTPACAPCTTTAPACACCAC | 4415-4435 | NC_001449 SEQ ID NO 34 |
| Forward-WEEm1 primer | CTAPTCCPCCAPCPAPC CAAGAACATAGCCTCTAA*G*G*C*G | 345-366 | NC_003908 SEQ ID NO 35 |
| Reverse-WEEm1 primer | CAGPAAGPGGTPGPTPG GCGTACACATCTTGGTATA*C*T*G*C | 482-460 | NC_003908 SEQ ID NO 36 |

TABLE 2-continued

Hybrid SAMRES-AEGIS primers and AEGIS (APTC) probes used in this study. All reverse primers are 5'-biotinylated; the probes are 5'-amino-C12- modified. The AEGIS tags in the primers are underlined.

| Oligos primers/probes | Sequences 5'-3' | Genome Region | GB Accession No. |
|---|---|---|---|
| WEE probe | TPTATPCACACAPACPCCAC | 418-437 | NC_003908<br>SEQ ID NO 37 |
| Forward-CE primer | CTAPTCCPCCAPCPAPC<br>CGGCATGATTGCAAAG*A*G*T*C | 675-694 | U12800<br>SEQ ID NO 38 |
| Reverse-CE primer | CAGPAAGPGGTPGPTPG<br>CGGAGCTTATGGCAACTTT*A*T*C*C | 792-770 | U12800<br>SEQ ID NO 39 |
| CE probe | PTTTPAPCPACACTPCTAPAAC | 731-752 | U12800<br>SEQ ID NO 40 |
| Forward JTC primer | CTAPTCCPCCAPCPAPC<br>CAACGATCTTACCATCCA*T*C*G*G | 283-304 | EF681804<br>SEQ ID NO 41 |
| Reverse JTC primer | CAGPAAGPGGTPGPTPG<br>CCATTGTTCCAATGAATGCC*A*T*T*G | 435-412 | EF681804<br>SEQ ID NO 42 |
| JTC probe1 | CAPAPAPAACTCATAAPPAPCAC | 365-387 | EF681804<br>SEQ ID NO 43 |
| JTC probe2 | PCACCATCATAAATCCAATTPCAPA | 384-408 | EF681804<br>SEQ ID NO 44 |
| Forward LAC primer | CTAPTCCPCCAPCPAPC<br>CACAGAGTCAAGCAAGG*C*A*T*G | 577-597 | NC_004110<br>SEQ ID NO 45 |
| Reverse LAC primer | CAGPAAGPGGTPGPTPG<br>GGCCTCCTTTTCCCCATT*T*A*A*G | 736-715 | NC_004110<br>SEQ ID NO 46 |
| LAC probe | PATPTCACAPAAPPTTPCAPC | 663-683 | NC_004110<br>SEQ ID NO 47 |
| Forward KS primer | CTAPTCCPCCAPCPAPC<br>GTGAGGACGAGTCACAA*A*A*G*G | 376-396 | U12801<br>SEQ ID NO 48 |
| Reverse KS primer | CAGPAAGPGGTPGPTPG<br>GAGATAGATTTCTACACCGT*T*G*C*C | 476-453 | U12801<br>SEQ ID NO 49 |
| KS probe | PATCAAPAPCACTPTCATCAATCC | 401-424 | U12801<br>SEQ ID NO 50 |
| Forward SSH primer | CTAPTCCPCCAPCPAPC<br>CCAAGAGCCTGAAGGAA*G*T*A*G | 687-707 | J02390<br>SEQ ID NO 51 |
| Reverse SSH primer | CAGPAAGPGGTPGPTPG<br>CCTTACTTATGGGAGCCT*G*A*T*G | 793-772 | J02390<br>SEQ ID NO 52 |
| SSH probe | PACACTPCCAPATCATTCTTPC | 740-761 | J02390<br>SEQ ID NO 53 |
| Forward 2 CA common primer | CTAPTCCPCCAPCPAPC<br>CGGTGCAAATGGATTTG*A*T*C*C | 112-132 (SA) | U47139<br>SEQ ID NO 54 |
| Forward 2 CA common primer | CTAPTCCPCCAPCPAPC<br>CGGTGCAAATGGATTTG*A*T*C*C | 111-131 (SN) | U47140<br>SEQ ID NO 54 |
| Reverse 1 CA common primer | CAGPAAGPGGTPGPTPG<br>GAGAGCAGCTTTGGCT*T*T*T*G | 235-216 (SA) | U47139<br>SEQ ID NO 55 |
| Reverse 1 CA common primer | CAGPAAGPGGTPGPTPG<br>GAGAGCAGCTTTGGCT*T*T*T*G | 234-215 (SN) | U47140<br>SEQ ID NO 55 |
| SA probe | CPATCAPTTTPTCTTCAPTTAPPATC | 174-199 | U47139<br>SEQ ID NO 56 |
| SN probe | CTTACAPCCPTTAPAATCTTCTTCC | 181-205 | U47140<br>SEQ ID NO 57 |
| Forward Mel primer | CTAPTCCPCCAPCPAPC<br>CTGAAGGATGTAGAGCA*G*C*T*G | 659-679 | U12802<br>SEQ ID NO 58 |

TABLE 2-continued

Hybrid SAMRES-AEGIS primers and AEGIS (APTC) probes used in this study. All reverse primers are 5'-biotinylated; the probes are 5'-amino-C12- modified. The AEGIS tags in the primers are underlined.

| Oligos primers/probes | Sequences 5'-3' | Genome Region | GB Accession No. |
|---|---|---|---|
| Reverse Mel primer | <u>CAGPAAGPGGTPGPTPG</u> GCCGAATTCATTAGAGGAC*C*A*T*C | 777-755 | U12802 SEQ ID NO 59 |
| Mel probe | capaapttcpptpttapacttcc | 725-747 | U12802 SEQ ID NO 60 |

PCR and Simulant Preparation

PCR targeting RNA virus simulants was set up in 1× JumpStart reaction buffer (10 mM Tris-HCl, pH 8.3; 50 mM KCl; 1.5 mM $MgCl_2$; 0.001% (w/v) gelatin) (Sigma-Aldrich, St. Louis, Mo.). The other components of the reaction mixture were (in a total volume of 100 μL): 2.5 ng/μL DNA oligo; 0.4 mM dNTPs; 0.4 μM each, Forward T7 primer and Reverse target-specific primer; JumpStart Taq DNA polymerase (2 units, Sigma), nuclease-free $ddH_2O$ (added to create a final volume of 100 μL). After the initial denaturation at 95° C. for 2 minutes, 35 cycles of amplification were performed (94° C. for 30 seconds, 55° C. for 30 seconds, and 72° C. for 1 minute). A final extension cycle was run at 72° C. for 5 minutes. Each PCR product (in 100 μL) was ethanol-precipitated and dissolved in nuclease-free dd $H_2O$ (12 μL). The resulting PCR products were sequenced in both directions (University of Florida, ICBR) and 5 pmol (about 2 μL) of the concentrated PCR product was used as a T7-DNA template to make RNA simulants.

For simulant production, a T7 RNA polymerase-dependent transcription reaction mixture (20 μL) was set up in a 1× transcription buffer (40 mM Tris, pH7.8, 20 mM NaCl, 18 mM $MgCl_2$, 2 mM spermidine HCl, 10 mM DTT). The reaction mixture contained ATP, CTP, GTP, and UTP (75 mM stock concentration 2 μL each), DNA template (2.5-5 pmol, purified and concentrated PCR product); T7 RNA polymerase (2 μL of a 200 U/μL to give 20 U/μL final concentration). Reaction mixtures were incubated at 37° C. for 8-12 hours. Turbo DNase was then added (2 U per reaction mixture, Life Technologies) to remove DNA template. The mixtures were then incubated at 37° C. for 15-20 minutes. RNA products were isolated by phenol-chloroform extraction and dissolved in nuclease-free water (20 μL). RNA products were resolved by 3% TBE agarose-gel electrophoresis and quantitated by their UV absorbance at 260 nm. The purity of RNAs was evaluated from their A260/A280 ratio. For pure RNA, a ratio of 1.8-2.1 is expected. The absence of template DNA in the RNA samples was confirmed by conventional PCR with Platinum Taq DNA polymerase (Life Technologies) and the ethidium-bromide gel. Samples were aliquoted and kept at −80° C.

Monoplex PCRs were first performed using each target RNA simulant separately to assess the efficacy of the primers in PCR cycling, as well as to determine the sensitivity of the assay. Reactions were then optimized under multiplexed conditions to minimize cross-amplification or cross-hybridization resulting from possible sequence similarity between targets.

Mono- and 21-Fold Multiplexed Nested One-Step RT-PCRs with SAMRS-AEGIS Primers

These were carried out in 1× Reaction mix (Life Technologies) with RNA simulant (4 ng/μL) in a final volume of 20 μL accordingly to the Invitrogen protocol for the SuperScript One-Step RT-PCR with Platinum Taq (Life Technologies). The reaction mixture contained 0.2 mM of dZTP; 0.025 μM each of 21 pairs forward and Reverse hybrid SAMRS-AEGIS target-specific primers; 0.25 μM External AEGIS Forward and Reverse-biotinylated primers; 2.5 units RT/Platinum Taq enzyme Mix. Additional 1.5 mM $MgSO_4$ were added to the RT-PCR buffer. Cycling conditions were: one cycle of the cDNA synthesis and pre-denaturation (53° C. for 30 minutes and 94° C. for 2 minutes), 55 cycles of PCR (94° C. for 15 seconds, 53° C. for 30 seconds, and 70° C. for 30 seconds) and final extension at 72° C. for 5 minute. A "no-target" PCR negative control was included with each assay run. To favor incorporation of biotin-labelled reverse primers to maximize hybridization sensitivity, the second PCR was performed with only reverse biotinylated primer (reverse primer extension reaction, RPER).

Digestion of Excess Primers and dNTPs

To destroy excess primers and deactivate dNTPs prior to RPER, ExoSAP-IT enzyme mixture (2 μL, Affymetrix, Cleveland, Ohio USA) were added to aliquots (5 μL) of standard or SAMRS-AEGIS nested PCR. Reaction mixtures were incubated at 37° C. for 30 minutes and the enzyme mixture was destroyed by heating at 80° C. for 20 minutes. Treated PCR products were added directly to the Reverse Primer Extension reaction.

Reverse Primer Extension Reaction (RPER)

Briefly, a RPER (20 μL) was set up in 1× ThermoPol Buffer (20 mM Tris-HCl, 10 mM $(NH_4)_2SO_4$, 10 mM KCl, 2 mM $MgSO_4$, 0.1% Triton X-100, pH 8.8 at 25° C.) with 3 μL of each ExoSAP-treated RT-PCR product, 5'-biotinylated external (common) Reverse AEGIS primer (0.2 μM), and Vent (exo-) DNA polymerase (1 unit NEB). Without conversion (an "extension" reaction), dNTPs (final 0.2 mM each) were added. For the dZ incorporation into the final amplicon ("conversion"), nucleoside triphosphates (dATP, dTTP, dGTP, and dZTP, final concentration 0.2 mM of each) were added. The "extension" and "conversion" reaction mixtures were incubated in s BioRad (DNA Engine) Peltier Thermal Cycler at 95° C. for 1 min, followed by 20 cycles (94° C. for 20 seconds, 55° C. for 30 seconds, 72° C. for 30 seconds). A final incubation was run at 72° C. for 1 minute. Reaction mixtures were then held at 4° C. and quenched with 4 mM EDTA.

For standard RT-PCR products, a set of 21 reverse target-specific primers (0.2 μM each) was added to the "extension" or "conversion" reactions. The other reaction components were the same as above.

Probe Coupling to Beads

Capture probes modified with an amino-C12 linker at the 5'-end were coupled to Luminex MicroPlex carboxylated micro-spheres ("beads") by a carbodiimide-based procedure according to the manufacturer's protocol. Briefly, for each combination of probe and bead set (Table 5), 2.5 million Luminex beads were resuspended in 0.1 M MES buffer (morpholine ethane sulfonic acid, 50 μL, pH 4.5) with probe (4 μL of 0.1 mM stock to give 0.4 nanomole final concentration), and treated twice with 1-ethyl-3-[3-dimethylamino-propyl]-carbodiimide hydrochloride (EDC, 5 μL of a 10 mg/mL solution, Thermo Scientific/Pierce, Rockford, Ill.) at room temperature for 30 min, rinsed in Tween 20 (0.02% aqueous solution), then rinsed with a sodium dodecylsulfate solution (0.1%), and resuspended in Tris-EDTA buffer (pH 8.0) to 5.0.

Luminex Direct Hybridization (DHA)

This was performed accordingly to the "no wash" Luminex protocol (http://www.luminexcorp.com/Support/SupportResources/). In a pilot experiment "wash" and "no wash" Luminex protocols were compared; no differences were found between two protocols when applied to our target-specific probes' design. Briefly, aliquots (5 μL) of each extension or conversion reaction were transferred to 96-well plates (96-well PCR thermo polystyrene plates; Costar). Hybridization buffer (25 μL of 2×Tm 0.4 M NaCl; 0.2 M Tris, 0.16 Triton X-100, pH 8.0) containing 100 of each target-specific probe-coupled microsphere set per μL or totally 2,500 target-specific probe-coupled each microsphere types. Microspheres were vortexed and sonicated for 20 seconds. The total volume was adjusted to 50 μL by 20 μl of $ddH_20$. 25 μl of $ddH_20$ were added to each Background well (negative control). Hybridization was performed at 55° C. accordingly to the direct hybridization protocol (DHA) provided by Luminex: 95° C. for 5 min, cool to 55° C. at a speed of 0.1° C./second, 15 mM at the hybridization T 55° C. Tm buffer (25 μL of 1×) containing streptavidin-R-phycoerythrin (2 μg, PJRS14, PROzyme) were added to the each hybridization mixture, which was then incubated at 56° C. for 5 min. Hybridization reactions were carried out in triplicate, and "no-target" controls were run in replicates of 6. Beads were analyzed for internal bead color and R-phycoerythrin reporter fluorescence using a Luminex 200 analyzer (Luminex xMAP Technology, Luminex Corporation) and the xPonent Software solutions. The median reporter fluorescence intensity (MFI) was computed for each bead type in the sample. The instrument's gate setting was established before the samples were run, and was maintained throughout the course of the study.

Results

Twenty-one mosquito-borne arboviruses were selected (Table 1) to assemble and develop xMAP Luminex assays diagnostic panel based on PCR amplification and using the artificial SAMRS-AEGIS technology [Yan10; Yan13].

Viral simulant RNAs were produced in vitro by transcription of the appropriate templates using T7 RNA polymerase. In pilot experiments, SuperScript One-Step RT-PCR with Platinum Taq (Life Technology) was found to be more sensitive and robust than other enzyme combinations tested, and thus able to support the nested PCR amplification with external primers containing the nonstandard P nucleotide, which pairs with the Z nucleotide. The target-specific standard or hybrid SAMRS-AEGIS forward and reverse primer pairs designed for the panel were tested first by monoplexed one-step RT-PCR with viral RNA simulants. Each monoplexed RT-PCR produced the expected amplicons, which were visualized by the ethidium-bromide staining following electrophoresis. Multiplexed RT-PCR conditions were established in a series of preliminary experiments (data not shown). Finally, multiplexed nested RT-PCRs were executed with each viral target using 21 pairs of specific SAMRS-AEGIS primers and AEGIS external primers (Table 2). PCR amplicons generated under optimized conditions were visualized on ethidium bromide gel as clearly resolved bands of the expected sizes ranging from 59 to 160 base pairs. The PCR negative control showed non-substantial level of primer-dimerization.

Amplicons containing only standard nucleotides were also produced by multiplexed one-step RT-PCRs and analyzed by agarose-gel electrophoresis. The 21-fold multiplexed reactions were primed with full set of target-specific primers, each at the final concentration of 0.4 The standard PCR amplicons were visualized on the ethidium bromide gel as clearly resolved bands of the expected sizes.

REFERENCES

[All98a] Allawi, H. T., SantaLucia, J. (1998) Nearest-neighbor thermodynamics of internal A•C mismatches in DNA: Sequence dependence and pH effects. *Biochemistry* 37, 9435-9444

[All98b] Allawi, H. T., SantaLucia, J. (1998) Thermodynamics of internal C:T mismatches in DNA. *Nucleic Acids Res.* 26, 2694-2701.

[Ben04] Benner, S. A. (2004) Understanding nucleic acids using synthetic chemistry. *Acc. Chem. Res.* 37, 784-797.

[Bro97] Brownie, J., Shawcross, S., Theaker, J., Whitcombe, D., Ferrie, R., Newton, C., Little, S. (1997). The elimination of primer-dimer accumulation in PCR. *Nucleic Acids Res.* 25, 3235-3241

[Col97] Collins, M. L., Irvine, B., Tyner, D., Fine, E., Zayati, C., Chang, C. A., Horn, T., Ahle, D., Detmer, J., Shen, L. P., Kolberg, J., Bushnell, S., Urdea, M. S., Ho, D. D. (1997) A branched DNA signal amplification assay for quantification of nucleic acid targets below 100 molecules/mL. *Nucl. Acids Res.* 25, 2979-2984

[Egh92] Egholm, M., Buchardt, O., Nielsen, P. E., Berg, R. H. (1992) Peptide nucleic-acids (PNA); Oligonucleotide analogs with an achiral peptide backbone *J. Am. Chem. Soc.* 114, 1895-1897

[Elb04a] Elbeik, T., Markowitz, N., Nassos, P., Kumar, U., Beringer, S., Haller, B. and Ng, V. (2004) Simultaneous runs of the Bayer VERSANT HIV-1 version 3.0 and HCV bDNA version 3.0 quantitative assays on the system 340 platform provide reliable quantitation and improved work flow. *J. Clin. Microbiol.* 42, 3120-3127

[Elb04b] Elbeik, T., Surtihadi, J., Destree, M., Gorlin, J., Holodniy, M., Jortani, S. A., Kuramoto, K., Ng, V., Valdes, R., Valsamakis, A. Terrault, N. A. (2004) Multicenter evaluation of the performance characteristics of the Bayer VERSANT HCV RNA 3.0 assay (bDNA) *J. Clin. Microbiol.* 42, 563-569

[Mar85] Martin, F. H., Castro, M. M., Aboul-ela, F., Tinoco, I. Jr. (1985) Base-pairing involving deoxyinosine—implications for probe design. *Nucl. Acids Res.* 13, 8927-8938.

[Mat98] Mathews, D. H., Andre, T. C., Kim, J., Turner, D. H., Zuker, M. (1998) An updated recursive algorithm for RNA secondary structure prediction with improved thermodynamic parameters. *Molecular Modeling of Nucleic Acids. ACS Symposium Series* 682, 246-257.

[Yan10] Yang, Z., Chen, F., Chamberlin, S. G., Benner, S. A. (2010) Expanded genetic alphabets in the polymerase chain reaction. *Angew. Chem. Int Ed.* 49, 177-180

[Yan13] Yang, Z., Durante, M., Glushakova, L. G., Sharma, N., Leal, N. A., Bradley, K. M., Chen, F., Benner, S. A. (2013a) Conversion strategy using an expanded genetic alphabet to assay nucleic acids. *Anal. Chem.* 85, 4705-4712

What is claimed is:

1. A template-directed process for extending one of a plurality of primers by enzymatic polymerization, wherein the template is one of a plurality of oligonucleotides, wherein said process comprises (a) contacting in aqueous solution the said plurality of primers with one or more of said oligonucleotides, a polymerase, and standard nucleoside triphosphates, and (b) incubating the mixture for a preselected length of time, wherein each of said primers has the structure:

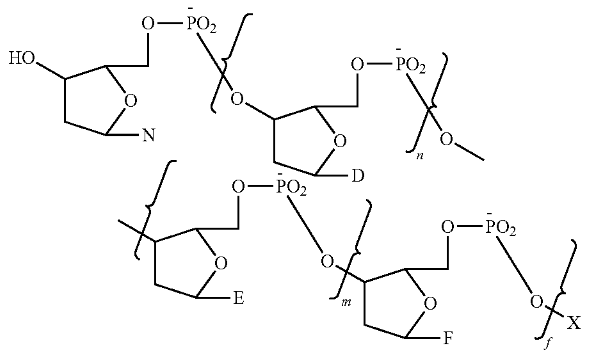

wherein X is selected from the group consisting of OH, O-phosphate, O-oligonucleotide, —$NH_2$, and a phosphate or an amino group linked to a biotin or a fluorescent tag, N is independently selected from the group consisting of adenine, thymine, guanine, cytosine, diaminopurine, uracil, A*, T*, G*, and C*, D is independently selected from the group consisting of A*, T*, G*, and C*, E is independently selected from the group consisting of A, T, G, and C, and F is independently selected from the group consisting of A, T, G, C, K, X, V, J, S, B, Z and P, wherein K, X, V, J, S, B, Z and P are the nucleobases disclosed in FIG. 1 or FIG. 2, wherein at least one F is selected from the group K, X, V, J, S, B, Z and P, wherein n is an integer from 4 to 6, m is an integer from 10 to 20, and f is an integer from 5 to 30, wherein the sequence of said primer at its 3'-end is substantially complementary to a portion of the sequence of one of said oligonucleotides, where A* does not contribute to the stability of a duplex when paired with T* but does when it is paired with thymine, T* does not contribute to the stability of a duplex when paired with A* but does when it is paired with adenine, G* does not contribute to the stability of a duplex when paired with C* but does when it is paired with cytosine, and C* does not contribute to the stability of a duplex when paired with G* but does when it is paired with guanine.

2. The process of claim 1 wherein A* is selected from the group consisting of 2-aminopurine and 2,6-diaminopurine.

3. The process of claim 1 wherein T* is selected from the group consisting of 2-thiothymidine and 2-thiouracil.

4. The process of claim 1 wherein G* is hypoxanthine.

5. The process of claim 1 wherein C* is selected from the group consisting of $N^4$-ethylcytosine and $N^4$-methylcytosine.

6. The process of claim 1 wherein the sum of m and n in said primers is at least 15.

7. The process of claim 1 wherein the D units are independently selected from the group consisting of T*, A*, G* and C*.

8. The process of claim 1 wherein the B units are independently selected from the group consisting of thymine, adenine, guanine, cytosine.

9. The process of claim 1 wherein A* is selected from the group consisting of 2-aminopurine and 2,6-diaminopurine.

10. The process of claim 1 wherein T* is selected from the group consisting of 2-thiothymidine and 2-thiouracil.

11. The process of claim 1 wherein G* is hypoxanthine.

12. The process of claim 1 wherein C* is selected from the group consisting of $N^4$-ethylcytosine and $N^4$-methylcytosine.

13. The process of claim 1 wherein more than 5 of said primer pairs are contacted.

14. The process of claim 1 wherein A* is either 2-aminopurine or 2,6-diaminopurine, G* is hypoxanthine, T* is either 2-thiothymidine or 2-thiouracil, and C* is either N-ethylcytosine or N-methylcytosine, n is between 4 and 6, F contains at least two nucleobases selected from the group consisting of K, X, V, J, S, B, Z and P, and N is either thymine, adenine, guanine, or cytosine.

15. A composition of matter that comprises a plurality of oligonucleotides, wherein each oligonucleotide having the formula

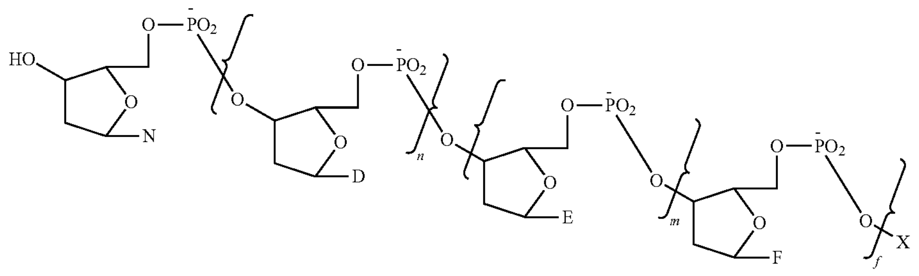

wherein X is selected from the group consisting of OH, O-phosphate, O-oligonucleotide, —$NH_2$, and a phosphate or an amino group linked to a biotin or a fluorescent tag, N is independently selected from the group consisting of adenine, thymine, guanine, cytosine, diaminopurine, uracil, A*, T*, G*, and C*, D is independently selected from the group consisting of A*, T*, G*, and C*, E is independently selected from the group consisting of A, T, G, and C, and F is independently selected from the group consisting of A, T, G, C, K, X, V, J, S, B, Z and P, wherein K, X, V, J, S, B, Z and P are the nucleobases described in FIG. 1 or FIG. 2, wherein at least one F is selected from the group K, X, V, J, S, B, Z and P, wherein n is an integer from 4 to 6, m is an integer from 10 to 20, and f is an integer from 5 to 30, wherein A* is either 2-aminopurine or 2,6-diaminopurine, G* is hypoxanthine, T* is either 2-thiothymidine or 2-thiouracil, and C* is either N-ethylcytosine or N-methylcytosine.

16. The composition of claim 15 wherein at least one D is selected from the group consisting of N-ethylcytosine and N-methylcytosine.

17. The composition of claim 15 wherein said oligonucleotides are dissolved in water at a concentration of 100 nanomolar or greater.

18. The composition of claim 15 wherein A* is either 2-aminopurine or 2,6-diaminopurine, G* is hypoxanthine, T* is either 2-thiothymidine or 2-thiouracil, and C* is either N-ethylcytosine or N-methylcytosine, n is between 4 and 6, F contains at least two nucleobases selected from the group consisting of K, X, V, J, S, B, Z and P, and N is either thymine, adenine, guanine, or cytosine.

* * * * *